United States Patent
Anwar et al.

[11] Patent Number: 6,030,368
[45] Date of Patent: Feb. 29, 2000

[54] POWER SYRINGE HAVING A BASE AND A LEVER

[75] Inventors: Azam Anwar, 4331 Arcady, Dallas, Tex. 75205; Christopher M. Boykin, Athens, Tex.

[73] Assignee: Azam Anwar, Dallas, Tex.

[21] Appl. No.: 08/959,679

[22] Filed: Oct. 29, 1997

Related U.S. Application Data

[63] Continuation-in-part of application No. 08/717,110, Sep. 20, 1996, Pat. No. 5,830,194.
[51] Int. Cl.[7] .............................. A61M 5/315; A61M 5/00
[52] U.S. Cl. ............................ 604/223; 604/228; 604/233
[58] Field of Search ............................ 604/72, 181, 187, 604/218, 223, 224, 228, 232, 233, 235, 131; 222/327

[56] References Cited

U.S. PATENT DOCUMENTS

| | | |
|---|---|---|
| 530,187 | 12/1894 | Laskey . |
| 900,565 | 10/1908 | Mayers et al. . |
| 2,200,012 | 5/1940 | Russel et al. ............................ 230/190 |
| 2,773,500 | 12/1956 | Young . |
| 4,014,331 | 3/1977 | Head . |
| 4,033,346 | 7/1977 | Phillips et al. ............................ 128/223 |
| 4,090,639 | 5/1978 | Campbell et al. . |
| 4,198,975 | 4/1980 | Haller ................................. 128/218 A |
| 4,737,151 | 4/1988 | Clement et al. . |
| 4,854,324 | 8/1989 | Hirschmann et al. . |
| 5,135,507 | 8/1992 | Haber et al. . |
| 5,228,883 | 7/1993 | Blakely et al. . |
| 5,288,285 | 2/1994 | Carter . |
| 5,336,201 | 8/1994 | von der Decken . |
| 5,350,365 | 9/1994 | De Godoy Moreira . |
| 5,352,203 | 10/1994 | Vallelunga et al. ....................... 604/110 |
| 5,368,578 | 11/1994 | Covington et al. . |
| 5,507,730 | 4/1996 | Haber et al. . |
| 5,591,135 | 1/1997 | Sullivan . |
| 5,749,853 | 5/1998 | O'Donnell et al. ....................... 604/97 |
| 5,814,017 | 9/1998 | Kashmer ................................. 604/110 |

FOREIGN PATENT DOCUMENTS

0409134 A1  1/1991  European Pat. Off. .

*Primary Examiner*—Corrine McDermott
*Assistant Examiner*—Michael J. Hayes
*Attorney, Agent, or Firm*—Tobor, Goldstein & Healey, L.L.P.

[57] ABSTRACT

An apparatus for delivering fluid, or power syringe, comprises a base, a lever, and a syringe. The syringe has a reservoir adapted for holding a quantity of fluid and a plunger disposed within the reservoir and adapted for movement therein. The reservoir features a clip on one end which releasably secures the end of the reservoir to the base and an inwardly facing annular flange on the second end which substantially prevents the plunger from being removed from the reservoir and substantially prevents leakage. The base of the apparatus features an extension beyond the end of the reservoir containing the clip, thereby providing stability to the apparatus during operation. The plunger features a clip on one end which releasably secures the plunger to the lever.

8 Claims, 3 Drawing Sheets

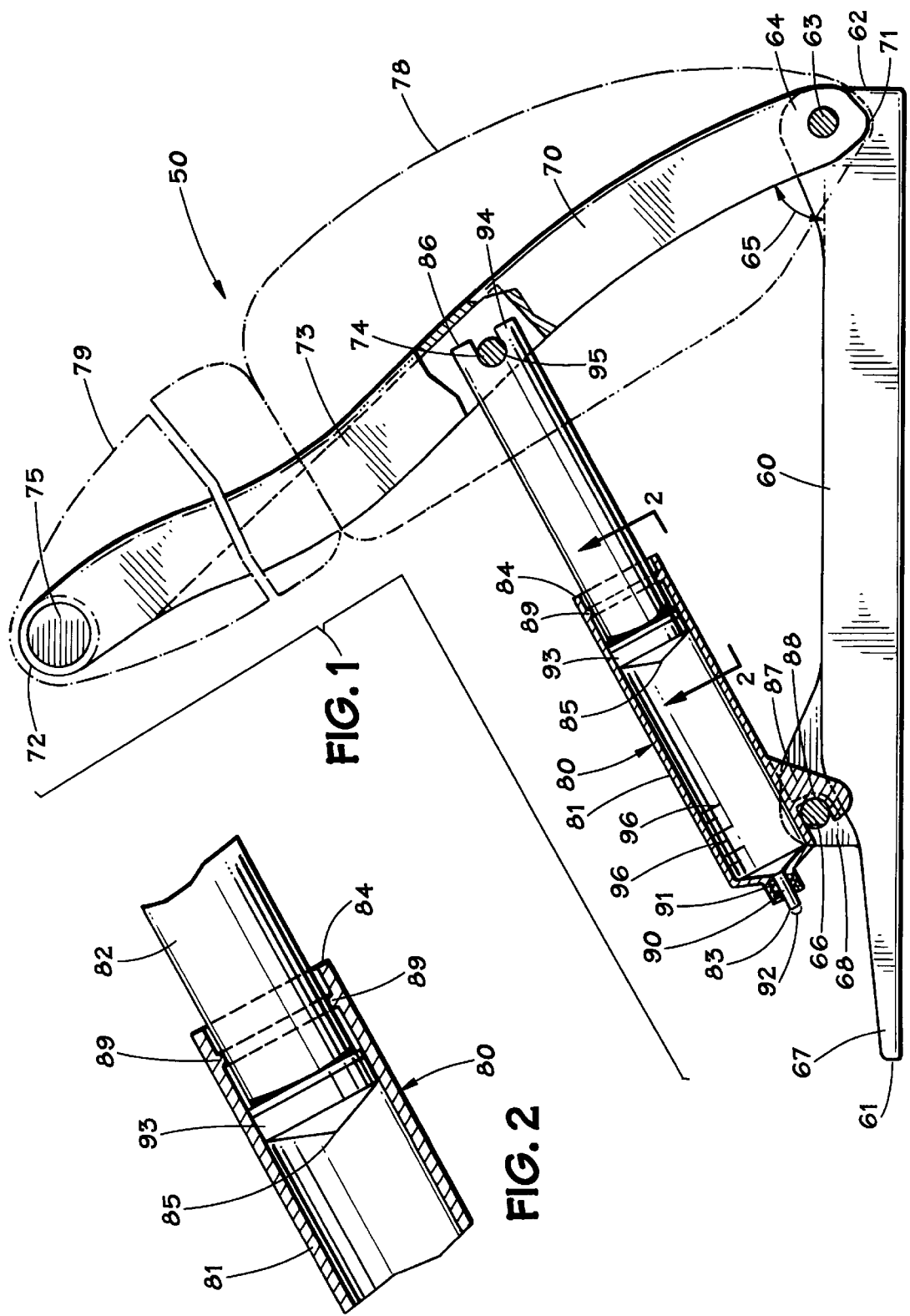

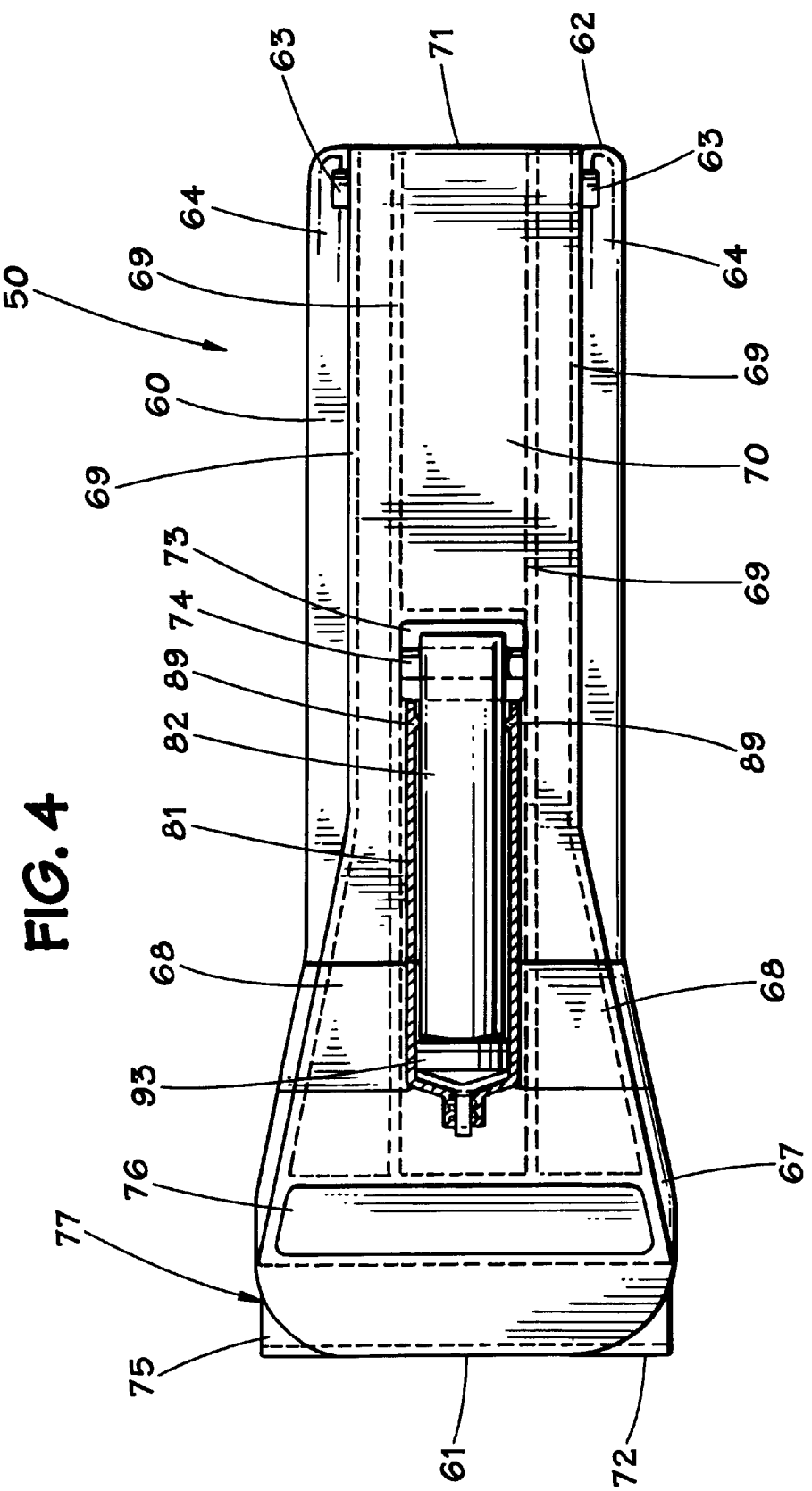

POWER SYRINGE HAVING A BASE AND A LEVER

RELATED APPLICATION

This application is a continuation-in-part application of application Ser. No. 08/717,110 filed Sep. 20, 1996, now U.S. Pat. No. 5,830,194.

FIELD OF THE INVENTION

The invention relates to an apparatus capable of delivering fluids, and more particularly a power syringe to inject contrast media or carbon dioxide into a patient during angiography.

BACKGROUND OF THE INVENTION

The invention relates to an apparatus capable of delivering fluid. More specifically, the present invention relates to angiographic devices, or power syringes, for injecting contrast media, such as x-ray dye, or carbon dioxide into a patient at a mechanically controlled rate and pressure during angiography. The objective of the angiogram x-ray must be twofold: (1) do not injure the patient, and (2) create the best angiogram x-ray possible. Patient discomfort, too much contrast media or carbon dioxide being delivered to a patient, and over-pressurizing the arteries are some of the problems of present angiographic devices. It is believed that the present invention will achieve these objectives and overcome the disadvantages of other devices in the field of the invention, but its results or effects are still dependent upon the skill and training of the operator.

While the following concentrates on the delivery of contrast media to a patient during angiography, it is to be understood that carbon dioxide, or other suitable gas which requires high pressurization for delivery, may be delivered to a patient by the present invention.

Prior coronary angiography procedures involved using either a hand-held syringe or a syringe driven by an electrically powered injector; however, both of these devices have deficiencies. Use of hand held syringes is limited to small arteries which require 5–7 cc of contrast media and do not require high pressure delivery. Angiography of large vessels and vascular chambers (left atrium, left ventricle, aorta, cerebral vessels, renal arteries, upper extremity vessels, vena cavae, lower extremity vessels, right atrium, right ventricle and pulmonary arteries) require more pressure, and thus more physical power than an operator can reasonably and effectively supply to hand-held syringes.

While use of an electrically powered angiographic injector system overcomes this deficiency of the hand held syringe, it still has several disadvantages. The electrically powered injector system is a large, cumbersome system that involves using either a 65 cc or a 130 cc syringe. It is cumbersome to load and unload, resulting in consistent waste of expensive contrast media. The syringe is loaded into the power drive mechanism and is filled with contrast media by drawing the contrast media into the syringe by moving the driving mechanism backward, which draws the contrast media into the syringe. Once loaded with contrast media, air, along with any particulate material, must be cleared from the system. The syringe is de-aired by jogging the screw drive of the machine forward and then physically beating the machine with your hand or a rubber hammer. The machine is then set to various control parameters. The most important parameter is the pressure setting. The electrically powered injectors have pressure settings from 150 to 1,200 psi. Once the machine is engaged, the contrast media is delivered at approximately the pressure setting dialed in. The contrast media cannot be easily stopped once the machine begins to operate. Because of the inability to modify the pressure setting during delivery, severe patient discomfort can result. Patient discomfort, such as the intense hot flash which is experienced frequently during angiography, is directly related to the contrast media being injected into the patient at pressures higher than necessary. Also, the sudden blast of injection can cause the catheter to become displaced or cause cardiac arrhythmia or injury to the vascular cavity.

The injection pressure of contrast media not only affects the comfort level of the patient, it also affects the clarity of the angiogram x-ray. Excessive contrast media will create a bright spot on the x-ray. Insufficient contrast media will create a dark spot on the x-ray. Therefore, it is very important that the proper amount of contrast media, as well as the pressure and rate at which it is delivered, be controlled for safe, desirable results.

Other syringe injectors also have certain disadvantages. One syringe injector includes a syringe which is held in place by a frame and the plunger is attached to a connecting rod extending from the back of the plunger to a lever attached to the frame. While this design overcomes some of the deficiencies of hand-held syringes, it is not designed for injecting contrast media into the larger vessels in vascular chambers of the circulatory system. Specifically, it does not prevent contrast media from leaking out of the back of the syringe reservoir which can occur under high pressures. It also requires the operator to pull forward, then push downward thereby preventing the operator from applying steady pressure and effectively controlling the delivery of contrast media. These devices require the operator to pull the lever forward and, then, once the lever has been moved to an angle less than 90° with the base, push down.

Accordingly, prior to the development of the present invention, there has been no apparatus for delivering fluid to a patient which: allows the operator to maintain control of the rate and pressure of delivery of the fluid, such as contrast media; assists in creating clear angiogram x-rays; and reduces patient discomfort. Therefore, the art has sought an apparatus for delivering fluid to a patient which: allows the operator to maintain control of the rate and pressure of delivery of the fluid, such as contrast media; assists in the creation of clear angiogram x-rays; and reduces patient discomfort.

SUMMARY OF THE INVENTION

In accordance with the invention the foregoing advantages have been achieved through the a present apparatus for delivering fluid to a patient, or power syringe. The present invention includes a base having first and second ends; a lever having first and second ends, with the first end of the lever being pivotally associated with the second end of the base; and a syringe having first and second ends, the syringe having open and closed positions, with the first end of the syringe being pivotally associated with the base and the second end of the syringe being pivotally associated with the lever and the lever defining an angle with the base which is less than 90° when the syringe is in the open position.

A further feature of the present invention is that the first end of the base may extend beyond the first end of the syringe.

In accordance with the invention the foregoing advantages have also been achieved through the present apparatus for delivering fluid to a patient, or power syringe. The present invention includes a base having first and second ends; a lever having first and second ends, with the first end of the lever being pivotally associated with the second end of the base; and a syringe having first and second ends, the syringe having open and closed positions, the syringe having a reservoir adapted for holding a quantity of fluid, wherein the reservoir has first and second ends, and a plunger disposed within the reservoir and adapted for movement within the reservoir, wherein the plunger has first and second ends, with the first end of the syringe being pivotally associated with the base and the second end of the syringe being pivotally associated with the lever, and the second end of the reservoir includes an inwardly facing annular flange in an abutting engagement with a portion of the plunger, whereby the flange substantially prevents leakage.

A further feature of the present invention is that the reservoir may include a clip which releasably secures the first end of the reservoir to the first end of the base. Another feature of the present invention is that the base may extend beyond the first end of the reservoir. An additional feature of the present invention is that the first end of the lever may be pivotally associated with the second end of the base, and defines an angle between the base and the lever which is less than 90° when the syringe is in the open position. Another feature of the present invention is that the ratio of the distance between the second end of the lever and the point of pivotal association of the second end of the plunger and the lever to the distance between the first end of the lever and the point of pivotal association of the second end of the plunger and the lever is greater than approximately 0.9. An additional feature of the present invention is that the lever includes first and second portions, the longitudinal axis of the first portion and the longitudinal axis of the second portion define an angle therebetween having a value less than, or equal to, 30 degrees. An additional feature of the present invention is that the first end of the reservoir may be pivotally associated with the first end of the base; and wherein the first end of the plunger is disposed within the reservoir and adapted for movement within the reservoir, and the second end of the plunger is pivotally associated with the lever.

In accordance with the invention, the foregoing advantages have also been achieved through the present syringe for use in an apparatus for delivering a fluid to a patient, the apparatus including a base and a lever. The syringe includes a reservoir adapted for holding the fluid, wherein the reservoir has first and second ends, wherein the first end of the reservoir includes a clip which releasably secures the first end of the reservoir to the first end of the base; and a plunger disposed within the reservoir and adapted for movement within the reservoir, wherein the plunger has first and second ends and wherein the second end of the plunger includes a means for securing the plunger to the lever.

A further feature of the syringe is that the second end of the reservoir may include an inwardly facing annular flange in abutting engagement with a portion of the plunger, whereby the flange substantially prevents leakage. Another feature of the syringe is that the second end of the plunger may include a clip which releasably secures the second end of the plunger to the lever.

The apparatus for delivering a fluid to a patient, and syringe for use in an apparatus for delivering fluid to a patient have the advantages of: allowing the operator to maintain control of the rate and pressure of delivery of the contrast media, thereby assisting in the creation of clear angiogram x-rays and reducing patient discomfort.

BRIEF DESCRIPTION OF THE DRAWINGS

In the drawings:

FIG. 1 is a partial cross-sectional side view of an embodiment of the power syringe of the present invention in an open position.

FIG. 2 is an enlarged partial cross-sectional side view of an inwardly facing annular flange taken along line 2—2 of FIG. 1.

FIG. 4 is a partial cross-sectional top view of the power syringe of FIG. 1 in a closed position.

Figure 3:
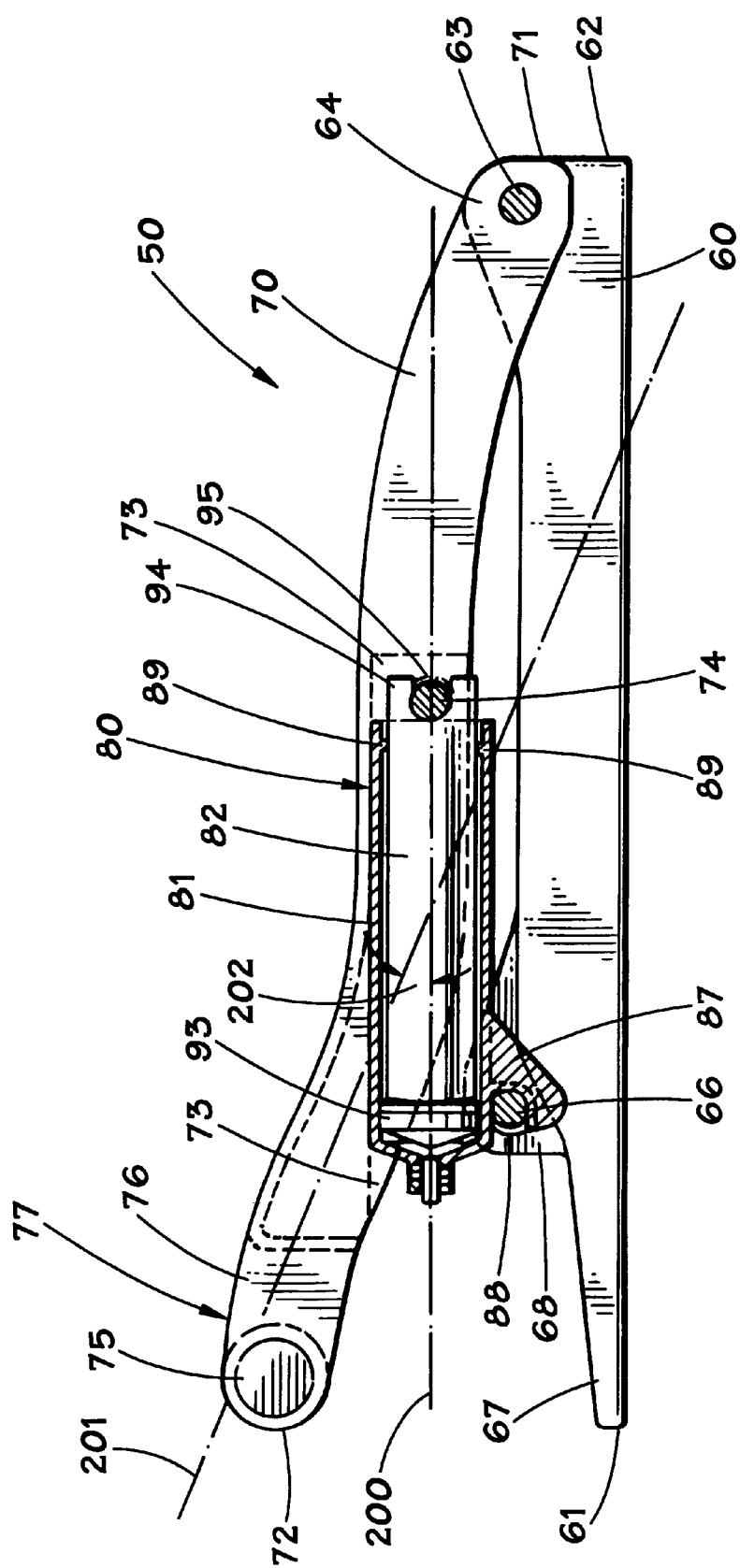
FIG. 3 is a partial cross-sectional side view of the power syringe of FIG. 1 in a closed position.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

In FIGS. 1–4, an apparatus for delivering fluid, or power syringe, 50, is disclosed. The present invention has been designed to assist in obtaining clear and detailed angiogram x-rays without sacrificing operator control which can result in patient discomfort. Power syringe 50 is shown to generally comprise a base 60, a lever or handle 70, and a syringe 80. Syringe 80 generally comprises a reservoir, or barrel 81, and a plunger, or piston 82. Power syringe 50 has an open position, as shown in FIG. 1, and a closed position, as shown in FIGS. 3 and 4. In its open position, lever 70 and base 60 define angle 65 which is less than 90°; and plunger 82 is withdrawn from reservoir 81 as shown in FIG. 1. In its open position, fluid (not shown) is taken into, and held in, syringe 80. In its closed position, lever 70 is pushed down and is substantially parallel with base 60; and plunger 82 is pushed forward into reservoir 81, as shown in FIGS. 3 and 4. As power syringe 50 moves from its open position to its closed position, fluid is expelled from syringe 80. Power syringe 50 allows the operator to control the delivery of fluid, or contrast media (not shown) to the patient, thereby achieving the objects of the invention of reducing patient discomfort and assisting in the creation of clear and detailed angiogram x-rays.

Power syringe 50 is designed to allow the re-use of base 60 and lever 70. Once the angiography procedure is completed, syringe 80 can be removed from base 60 and lever 70 and disposed. Base 60 and lever 70 can then be sterilized and a new, sterile, syringe 80 can be placed in power syringe 50 and used in another angiography procedure.

As illustrated in FIGS. 1, 3 and 4, base 60 has a first end 61 and a second end 62. Lever 70 has a first end 71 and a second end 72; and a first portion represented by region 78 shown in phantom lines in FIGS. 1 and 3; and a second portion represented by region 79 shown in phantom lines in FIGS. 1 and 3. Lever 70 includes a transversal opening 75 and a slot 76 which define a hand grip 77 which enable the operator to more easily grip lever 70 and apply the necessary force to deliver the contrast media. Preferably, hand grip 77 is wide enough to accommodate the operator's hand, thereby preventing injury to the operator's hand and wrist. Preferably, the width of hand grip 77 is approximately from at least 3 inches to approximately 6 inches. Preferably, the longitudinal axis 200 of first portion 78 and the longitudinal axis 201 of second portion 79 define an angle 202 (FIG. 3) therebetween having a value of approximately 30° or less, thereby preventing lever 70 and the operator's hand from interfering with attachments (not shown) to first end 83 of syringe 80 as lever 70 is pushed downward. Angle 202 may be less than 30° if provisions are made to prevent lever 70 and the operator's hand from interfering with any attachments to first end 83 of syringe 80. Preferably angle 202 is not greater than approximately 30°, an angle greater than approximately 30° may create excessive strain on the operator's wrist as lever 70 is pushed downward. First end 71 of lever 70 is pivotally associated with base 60 as by use of a pin 63 at the second end 62 of base 60. Lever 70 is pivotally associated with base 60 at a raised portion 64 of base 60 at second end 62 of base 60. The syringe 80 is disposed between lever 70 and base 60; and lever 70 and base 60 define angle 65 which is approximately 90° or less, when power syringe 50 is in its open position. In the preferred embodiment shown in FIG. 1, angle 65 is about 60° when power syringe 50 is in its open position. Angle 65 is advantageous in the high pressure delivery of contrast media because of the downward direction of applied force to move power syringe 50 from its opened position to its closed position. This one direction application of force prevents power syringe 50 from lifting up off the table or other surface where it has been placed for use. In its closed position, syringe 80 is received within a recess 73 formed in lever 70 as shown in FIGS. 3 and 4.

Still with reference to FIGS. 1, 3 and 4, syringe 80 has a reservoir, or barrel, 81 adapted for holding a quantity of fluid, such as contrast media, and a plunger 82 disposed within reservoir 81 and adapted for movement within reservoir 81. Reservoir 81 has first end 83 and second end 84 and is pivotally associated with base 60. Plunger 82 has first end 85 and second end 86 and is pivotally associated with lever 70 between first end 71 and second end 72 of lever 70 as by use of a pin 74. Thus, when lever 70 is moved downwardly, plunger 82 moves forward within reservoir 81, thereby delivering the fluid, by forcing it outwardly through opening 92. The mechanical lever 70 amplifies the operator's downward force on plunger 82, thereby creating greater injection pressure. Preferably, the ratio of the distance between second end 72 and pin 74 to the distance between first end 71 and pin 74 is greater than one, thereby creating a greater power advantage and allowing delivery of fluid at higher pressures. The operator may control the delivery of contrast media by increasing or decreasing the amount of downward force on lever 70.

With reference to FIG. 1, reservoir 81 has a luer 90 encompassed by a stationary threaded connector 91 on first end 83 of reservoir 81. Luer 90 has an opening 92 through which fluid passes into, and out of, reservoir 81. Luer 90 is connected to a catheter (not shown) through which fluid, or contrast media, is delivered to a patient. Reservoir 81 preferably is made out of a clear or partially transparent material so that the fluid contained therein is visible, such as any suitable plastic material having the requisite strength characteristics to operate as power syringe 50, as well as being capable of being used in an operating or laboratory sterile environment. For example, if syringe 80 is constructed out of conventional syringe material, the wall of reservoir 81 will need to be thicker than the wall of syringes constructed out of the same conventional material in order to withstand the high pressure forces required for delivery. Also, a series of column indicators 96 may be marked on the surface of reservoir 81 to indicate the column of fluid contained within reservoir 81 and allow the operator to monitor the volume of contrast media being injected.

With reference to FIGS. 1 and 3, reservoir 81 has clip 87 on the underside of first end 83 of reservoir 81, forming an opening 88 to releasably secure syringe 80 to base 60. Although one clip 87 is illustrated in FIGS. 1 and 3, more than one clip 87 may be on the underside of first end 83 of reservoir 81 to provide the required strength necessary to releasably secure syringe 80 to base 60. Clip 87 on first end 83 of reservoir 81 allows reservoir 81 to be releasably secured to base 60. Clip 87 allows syringe 80 to be removed and replaced after use. Clip 87 is designed to insure that reservoir 81 remains pivotally secure to base 60 during use. Clip 87, and thus reservoir 81, is secured to base 60 by snapping clip 87 onto pin 66 in base 60. Preferably clip 87 is formed integral with reservoir 81.

As illustrated in FIGS. 1 and 2, reservoir 81 has an inwardly facing annular flange 89 at second end 84 of reservoir 81. Inwardly facing annular flange 89 at second end 84 of reservoir 81 substantially prevents plunger 82 from being removed from reservoir 81 and substantially prevents leakage. Inwardly facing annular flange 89 is in an abutting engagement with a portion of plunger 82, thereby providing a stronger connection between plunger 82 and reservoir 81, which allows power syringe 50 to withstand the amount of downward force necessary to deliver fluid, or contrast media, without concern for fluid, or contrast media, leaking behind plunger 82 and out of reservoir 81. Inwardly facing annular flange 89 also provides a safety function by substantially preventing plunger 82 from being forced out of reservoir 81 as a result of the high fluid pressure forces contained in power syringe 50 which could act to force plunger 82 outwardly of reservoir 81. This could occur if the operator's hand is accidentally released from lever 70 while applying a force to lever 70. While inwardly facing annular flange 89 is shown in FIGS. 1–4 as being substantially rigid, inwardly facing annular flange 89 may be a resilient annular flange, such as a rubber gasket, or O-ring, disposed within reservoir 81. Preferably, inwardly facing annular flange 89 is formed integral with reservoir 81.

As illustrated in FIGS. 1, 3 and 4, plunger 82 has a diameter substantially equivalent to the inner diameter of reservoir 81, thereby providing more power advantage for delivery of fluid under high pressure forces, and substantially preventing fluid from leaking behind plunger 82 and out of reservoir 81. Plunger 82 has rubber tip 93 at first end 85 of plunger 82. Preferably, rubber tip 93 has a diameter approximately the same size as, or slightly greater than, the inner diameter of reservoir 81 thereby allowing delivery of fluid at higher pressures and substantially preventing fluid from leaking out of reservoir 81. Plunger 82 has clip 94 forming an opening 95 on second end 86 of plunger 82 which allows plunger 82 to be pivotally secured to lever 70 as by a pin 74 in lever 70. Plunger 82 is disposed within reservoir 81 and is adapted for movement within reservoir 81. Clip 94 on the second end 86 of the plunger 82 releasably secures plunger 82 to lever 70. Clip 94 allows plunger 82 to be removed and replaced after use. Clip 94 is designed to insure that plunger 82 remains pivotally secured to lever 70 during use. Clip 94 is secured to lever 70 by snapping clip 94 onto pin 74 in lever 70. Preferably, clip 94 is formed integral with plunger 82.

As illustrated in FIGS. 1 and 3, power syringe 50 also features an advantageously designed base 60. Base 60 is preferably wider than syringe 80 and lever 70, thereby preventing power syringe 50 from tilting sideways during use upon the application of a substantial downward actuating force upon lever 70. Base 60 has an extension member 67 extending beyond first end 83 of reservoir 81. Extension member 67 of base 60 widens as it continues beyond first end 83 of reservoir 81. Extension member 67 allows power syringe 50 to remain stable under operating conditions which require extreme downward force on lever 70, without the concern that power syringe 50 will slip or move in such a way that the connection to the catheter is broken, such as by base 60 and lever 70 tipping over, or rotating about the pivoted connection at pin 66 and clip 87. Extension member 67 also provides an area for the operator to apply downward force to base 60 to stabilize and/or steady power syringe 50 while moving power syringe 50 from its closed position to its open position. Base 60 preferably includes raised area 68 at first end 61 of base 60 where reservoir 81 is pivotally secured with base 60. Base 60 may also include raised area 64 at second end 62 of base 60 where lever 70 is pivotally associated with base 60. Raised area 64 and raised area 68 allow first end 83 of reservoir 81 to pivot without interference from base 60. Base 60 may include reinforcing ribs 69 molded into base 60 (FIG. 4). Base 60 may also be adapted to increase the friction between base 60 and the surface on which power syringe 50 is placed thereby preventing power syringe 50 from slipping and/or sliding with respect to the surface upon which it is supported during use. For example, the underside of base 60 may have corrugated or roughened surface, or may be coated with a material which prevents slippage.

Of course it will be readily apparent to one of ordinary skill in the art that other connection means could be used other than pins 66 and 74 to releasably secure syringe 80 with lever 70 and base 60. Additionally, clip 87 may be disposed on base 60 and pin 66 may be disposed on syringe 80; and clip 94 may be disposed on lever 70 and pin 74 may be disposed on syringe 80.

It will also be readily apparent to one of ordinary skill in the art that power syringe 50 may be constructed out of numerous different materials. Preferably, reservoir 81 and lever 70 of power syringe 50 are constructed out of transparent plastic, thereby allowing the operator to view column indicators 96 and monitor the volume of fluid in reservoir 81. Any other material providing the required strength and durability characteristics necessary to perform the functions of power syringe 50 may be used to construct any or all of the components of power syringe 50, such as metals or plastic materials.

To operate power syringe 50, the operator loads syringe 80 by pushing up on lever 70 which pulls back, or withdraws, plunger 82 to bring fluid, or contrast media, into reservoir 81 by creating a vacuum in reservoir 81. Syringe 80 is de-aired by turning power syringe 50 upside down, thereby allowing air to rise to first end 83 of reservoir 81, where it is expelled by pushing on lever 70, which in turn, pushes plunger 82 forward until all air is removed. It is then attached to a three-way stopcock (not shown). The operator can then press down on lever 70 while watching the fluoroscope (x-ray machine). The operator can create a better angiogram x-ray by pressing down harder on lever 70 to create higher pressure and release more contrast media. Also, the operator can stop the procedure if the patient is experiencing discomfort. The pressure applied by the operator to lever 70 translates into the pressure in which contrast media is delivered to the patient. The more force the operator applies by pushing down on lever 70, the higher the pressure at which the fluid, or contrast media, is delivered. Therefore, the operator can modify the amount of contrast media necessary for the x-ray during the angiography procedure.

It is to be understood that the invention is not limited to the exact details of construction, operation, exact materials, or embodiments shown and described, as obvious modifications and equivalents will be apparent to one skilled in the art. For example, clip 87 may fully encompass pin 66, thereby requiring pin 66 to be removed before syringe 80 is removed and replaced. Likewise, clip 94 may fully encompass pin 74, thereby requiring pin 74 to be removed before syringe 80 is removed and replaced. Another obvious modification and equivalent would be an extended or modified lever 60 which further assists the operator in applying the amount of force necessary to deliver fluid to a patient. An additional modification and equivalent would be an inwardly facing flange 89 disposed within reservoir 81 by a removable cap which is securely attached to second end 84 of reservoir 81. Accordingly, the invention is therefore to be limited only by the scope of the appended claims.

What is claimed:

1. An apparatus for delivering fluid to a patient comprising:

a base having first and second ends;

a lever having first and second ends, with the first end of the lever being pivotally associated with the second end of the base; and a syringe having first and second ends, the syringe having a reservoir for holding a quantity of fluid, wherein the reservoir has an underside and first and second ends, and a plunger slidably disposed within the reservoir for movement within the reservoir, wherein the plunger has first and second ends, with the first end of the syringe being pivotally associated with the base and the second end of the syringe being pivotally associated with the lever, and the first end of the reservoir includes a clip which releasably secures the first end of the reservoir to the first end of the base, the clip being disposed on the underside of the reservoir, thereby permitting the reservoir to pivot with respect to the base.

2. The apparatus of claim 1, wherein the first end of the base extends beyond the first end of the reservoir.

3. The apparatus of claim 2, wherein the first end of the lever is pivotally associated with the second end of the base, defining an angle between the base and the lever which is less than 90 degrees when fluid is taken into, and held in, the syringe.

4. The apparatus of claim 3, wherein the second end of the plunger includes a clip which releasably secures the second end of the plunger with the lever.

5. The apparatus of claim 4, wherein the first end of the reservoir is pivotally associated with the first end of the base; and wherein the first end of the plunger is slidably disposed within the reservoir for movement within the reservoir, and the second end of the plunger is pivotally associated with the lever.

6. The apparatus of claim 1, wherein the first end of the lever is pivotally associated with the second end of the base, defining an angle between the base and the lever which is less than 90 degrees when fluid is taken into, and held in, the syringe.

7. The apparatus of claim 6, wherein the second end of the plunger includes a clip which releasably secures the second end of the plunger with the lever.

8. The apparatus of claim 7, wherein the first end of the reservoir is pivotally associated with the first end of the base; and wherein the first end of the plunger is slidably disposed within the reservoir for movement within the reservoir, and the second end of the plunger is pivotally associated with the lever.

* * * * *